United States Patent [19]

Distl et al.

[11] Patent Number: 4,671,660

[45] Date of Patent: Jun. 9, 1987

[54] DUAL-BEAM-REAL-TIME POLARIMETER

[76] Inventors: Richard Distl, Edlingerstr. 7, D-8000 München 90; Ulrich Schmidt, Heerstr. 8, D-1000 Berlin 19, both of Fed. Rep. of Germany

[21] Appl. No.: 779,247

[22] Filed: Sep. 23, 1985

[30] Foreign Application Priority Data

Sep. 25, 1984 [DE] Fed. Rep. of Germany ....... 3435189
Dec. 7, 1984 [DE] Fed. Rep. of Germany ....... 3445318

[51] Int. Cl.$^4$ .............................................. G01J 4/04
[52] U.S. Cl. .................................... 356/367; 356/368
[58] Field of Search ............... 356/364, 365, 366, 367, 356/368, 369, 370

[56] References Cited

FOREIGN PATENT DOCUMENTS

84/03357 8/1984 PCT Int'l Appl. ................. 356/367

Primary Examiner—Eugene R. LaRoche
Assistant Examiner—Steven J. Mottola
Attorney, Agent, or Firm—Kinney & Lange

[57] ABSTRACT

A device for measuring the rotation of the plane of vibration of linearly polarized electromagnetic radiation includes a beam splitter that divides the radiation into beams following a measurement beam path and a reference beam path, and each of the beam paths are analyzed after interaction with a reference element and a sample to be measured. The beams impinge upon photosensitive sensors and the output signal from such sensors is processed to determine the characteristics of the sample that are desired to be analyzed.

9 Claims, 2 Drawing Figures

DUAL-BEAM-REAL-TIME POLARIMETER

DESCRIPTION

The present invention relates to a device for the measurement of the rotation of the plane of vibration of linearly polarized radiation caused by optically active substances.

In an arrangement for measuring in accordance with the invention, each of the measured values of the rotation for the sample is always standardized against the optical activity of a reference substance determined in a reference beam of radiation. In this way the result of the measurement is always free from the influences of the wave length used for the measurement and/or from the temperature. The determination of the plane of vibration under these conditions is effected in real time.

A measuring device in accordance with the characterizing features of the patent claims may, for example, be utilized in all those situations where the circular double refraction or birefringence or its dynamic changes are required to be measured rapidly with great accuracy. Thus, for example, it may be used in polarimetry for the determination of the concentration, the layer depth, or the specific rotation of optically active substances.

PRESENT STATE OF THE ART

A multi-beam measuring device for polarimetric investigations of test samples in real-time procedures is described in the PCT-Application PCT/EP84/00050 (SCHMIDT DISTL).

The inventive teachings of the above-named PCT/EP84/00050 rest upon, amongst other things, the fact that the direction of vibration of the light beam may be calculated from the determination of the ratio of the relative intensity of the light beam to be analyzed, after it emerges from an analyzer, to its absolute intensity before entering the analyzer. For this purpose, the beam of light after passing through the test sample is divided up by means of a beam divider, preferably a diffraction grating, into a reference beam and at least one test beam in the path of which an analyzer with fixed direction of transmission is located. The intensities of the part beams are determined by means of the photosensitive sensor which is allocated to each of the beams. The signal outputs of the photosensitive sensors are connected to the inputs of a measuring circuit for the determination of the polarimetric values assignable to the test sample.

The measuring circuit is constructed essentially as follows: By means of a temporary storage which is coupled in after each of the photosensitive sensors, the output signals from the photosensitive sensors are stored synchronously and for a short time. A control circuit which is allocated to the temporary storages assumes control of the temporary storage. The formation of the ratio of the relative intensity to the absolute intensity is effected by means of a delay-free operating division circuit, which is connected on its input side to the output of the temporary storage. For the calculation and the output of the polarimetric values assignable to the test sample, in particular the optical activity, a digital data processing device is provided, which is connected on its input side to the output from the division circuit. In addition to this, the measuring circuit is provided with at least one A/D-converter which converts the analog signals to digital form for further processing.

In the above-named multi-beam measuring device, the method of operating of the beam divider assumes decisive importance with respect to the accuracy of measurement.

Dielectric beam dividers, for example, are not suitable because their dividing ratio is a function of the direction of vibration of the incident light beam. Consequently, the falsifying mode of operating of this beam divider also enters into the measurement results.

In the afore-mentioned PCT/EP84/00050, a proposal is made in this regard to use a diffraction grating as the beam divider element. Under these conditions, it is of primary importance to ensure that the beam of light incident on the diffraction grating always strikes the grating structure in exactly the same way, because the diffraction efficiency is a function of the angle of incidence.

Consequently, an adequate concentration of the light source at a point must be striven for, which can only be achieved by an expensive system for guiding the path of the beam. A further disadvantage resides in the fact that considerable losses of light are involved in this procedure. Since the direction of vibration of the reference beam is not defined, the measurement result is further falsified by the vector sensitivity of the photosensitive sensor allocated to the reference beam.

It is already known from the European Patent Application No. 80106584.8 (MULLER) that the beam divider and the analyzer within a polarimeter may be incorporated together into a plane-parallel plate of a glass prism, for example.

These elements can, most certainly, with certain limitations, as intended in this Application, serve as demodulators but they are, however, as will be described at a later stage, not suitable as a beam divider within a measuring device for the quantitative determination of the polarization state of electromagnetic radiation.

The transmitted portion of the radiation is only partly polarized by these types of elements, that is to say, the desired function of the analyzer is very substantially inhibited. This fact is of importance in so far as the measuring accuracy of a measuring device having the elements as described is directly limited thereby. Furthermore, the degree of polarization of the reflected radiation substantially depends upon the angle of incidence of the incident light beam. This applies particularly in the region of the Brewster angle. In relation to this it should be noted that, for example, during the investigation of test samples, the measuring beam will rarely impinge on the divider element at a constant angle, for the simple reason that the molecular structure or the inhomogeneity of the test sample leads to an unavoidable partial deflection of the measuring beam. This means that the degree of polarization of the reflected radiation is altered to an indeterminate extent.

Accordingly, the measured values determined by means of a measuring device, with the elements as described in the foregoing section for the purpose of beam division and simultaneous use as an analyzer, are encumbered with two systematic errors of measurement A polarimetric measuring device is described in the German Offenlegungsschrift No. P 22 61 875.3 (SIEMENS AG) in which a polarizing double prism is employed as beam divider and analyzer.

Here the great disadvantage is the fact that, with a double prism—for example a Wollaston prism—the angle of divergence of the emergent part beams is dependent upon the wave length of the incident radiation.

Because the photosensitive sensors which are provided to detect the intensity of the part beams are, as a general rule, mounted in a stationary position, their utilization for variable or indeterminate wave lengths of the radiation to be analyzed is accordingly not possible.

Furthermore, in the case of a double prism, the two radiation components do not emerge from the crystal in a direction perpendicular to its surface of emission, which means that different reflection and absorption losses occur, and these falsify the measurement results.

A procedure for measuring the optical activity of a test sample is described in the European Patent Application No. EPA 0 087 535 (American Crystal Sugar Company). In this case, the radiation emitted from an IR-light source is linearly polarized and passes through the sample chamber subsequently to impinge upon a beam dividing analyzer. This splits up the radiation into its polarized components which are perpendicular to one another, following which they are picked up by separate photo-receivers. The signals are transmitted, by way of an amplifier with adjustable offset and amplification, to a divider. The division signal is fed into an evaluation unit, which determines the result of the measurement by reference to empirical Tables.

The temperature of the test sample is determined by means of a sensor. If no data are available concerning the temperature dependence of the optical activity, it is not possible to use any compensation for temperature. The basic Tables used with the measurement results for compensation of non-linearity are different for individual measuring instruments because, for example, the degree of polarization of the totally-reflected components in the beam dividing analyzer is not a physical constant.

The adjustment of the offset and amplification of the operations amplifiers is effected by means of variable resistances. With the sought-after accuracy of the 16-bit resolution, the result cannot be stable for long periods of time, because there are no structural components available whose drift and thermal behavior lie within the tolerances which are required for it. The absorption by the test sample is therefore compensated for by means of intensity control of the light source. This signifies that the dynamic range of the measuring system is limited by the dynamic range of the light source.

In all of the previously discussed procedures for the measurement of the optical activity of a test sample, any deviation of the measurement temperature and the measurement wave length from the reference specification has a direct influence upon the results of the measurements. A knowledge of the actual conditions of these various parameters—the ORD-(optical rotatory dispersion)-spectrum, as well as the temperature dependence—is then, however, essential for the determination of values derivable from the optical activity.

DISCLOSURE OF THE INVENTION

Figure 1:
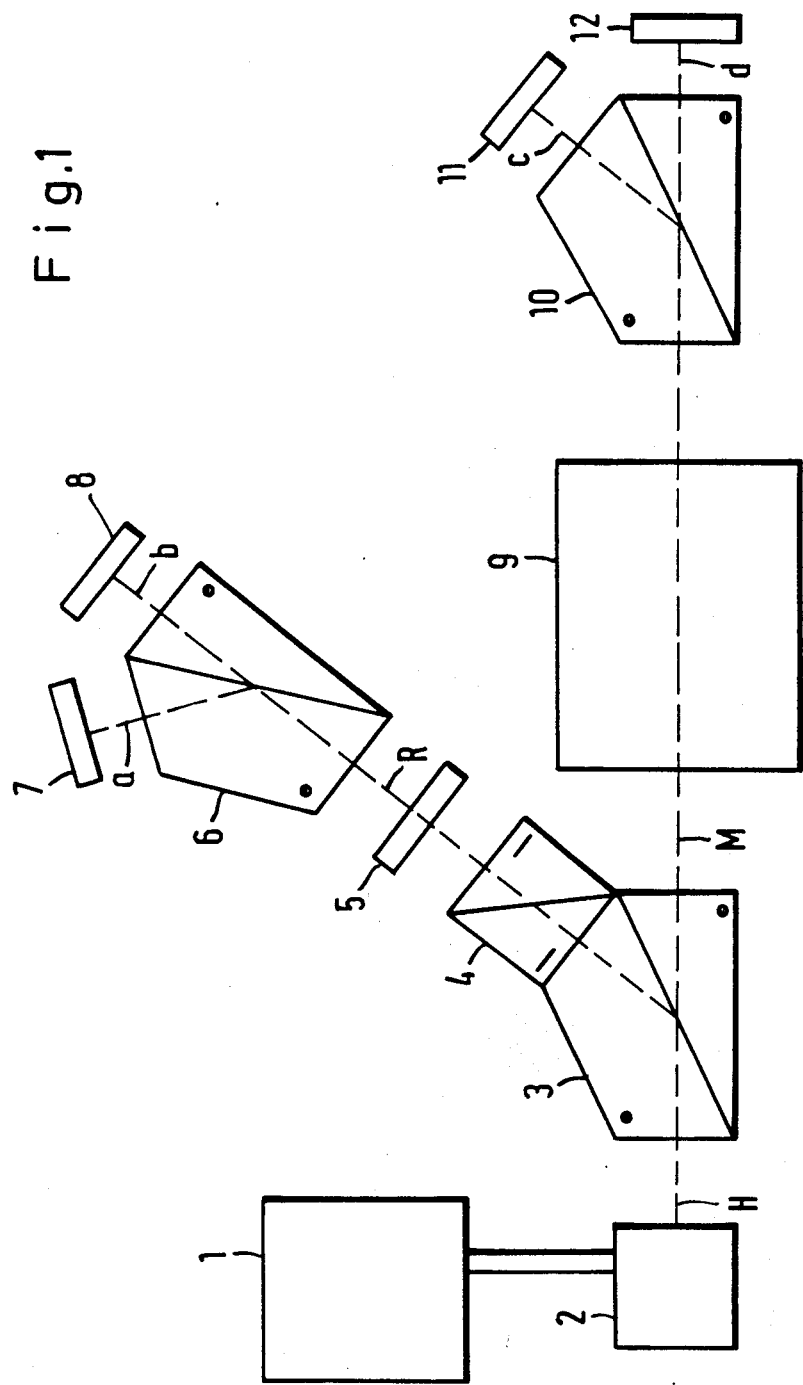
FIG. 1 depicts an embodiment of the optical section of the invention.

The teachings of the present invention are concerned essentially with the further development of the measuring arrangement of the type known from the PCT/EP84/00050, with respect to both function and accuracy of measurement, in which case it is particularly the problems which were initially referred to in the said PCT/EP84/00050 that are to be solved in a technically effectual and simple manner.

The problems which have been posed are solved in accordance with the patent claims made for the invention.

The electromagnetic radiation emanating from the light source is split up into a measuring beam path and a reference beam path before its interaction with the substance under investigation. Under these circumstances, the reference beam, after interaction with a reference element, impinges on a first beam-dividing analyzer, and the measuring beam, after interaction with the test sample under investigation, impinges on a second beam-dividing analyzer.

The beam-dividing analyzers consist of a birefringent material, which means that the two part beams emerge at different places from this element. Each one of these part beams has a photosensitive sensor allocated to it, under which conditions these are connected on their output side with the inputs to a measurement circuit. This measurement circuit possesses temporary storages coupled in after each photosensitive sensor, and these store the output signals from the photosensitive sensors synchronously and for a short period of time only. In this way, identical measurement conditions are guaranteed during the course of the measurement. Furthermore, for determination of the absolute intensity, the measurement circuit is furnished with addition-circuits which are coupled-in before the beam-dividing analyzers, as well as a division-circuit allocated to each beam path, and this is connected at its input side with the output from the addition-circuit allocated to the relevant beam path, and to the output of one of the two temporary storages to which the addition-circuit is allocated. This supplies a standardized output signal which, in particular, is independent of the output intensity of the light source and the absorption of the test sample under investigation or that of the reference element. The output signals from the two division-elements are selectively supplied to a digital data-processing device by way of an analog circuit. In addition to this, there is at least one analog/digital converter for this purpose coupled-in before the digital data-processing device. As the result of this, a further processing of the measurement signals is possible in real time.

The teachings of the invention describe a measuring arrangement which allows for the application of the dual-beam principle which is already known from other domains of measurement techniques, for example, spectroscopy and photometry, within the field of polarimetry. Here too it is fundamentally a matter of eliminating the influence of certain measurement-result-falsifying parameters, which are inherent in the system, from affecting the measurement results.

The optical activity or the values derivable from it, such as those to be determined by polarimetry are, amongst other things, functions of the temperature of the substance under investigation and the wave length of the radiation which is to be passed through the substance. These two parameters can only be kept stable and constant at a specified value, within the strict tolerances demanded by precision polarimetry ($+/-0.01°$ C. $+/-0.1$ mm deviation from the effective wave length) during the period of measurement, at very considerable expense. In many applications it is quite impossible to keep within such narrow tolerance limits. This is the case, for example, when using transmitter diodes whose peak wave lengths vary greatly because of thermal effects and dependence upon the power output.

The dependence upon wave length and temperature, as referred to previously, is eliminated by the dual-beam measurement procedure in accordance with the invention by having the optical activity of the substance being analyzed—that is to say, the rotation of the plane of vibration caused by the substance—standardized during every measuring cycle, with respect to the reference wave length and the temperature, by means of a correction factor which is determined in the reference beam. Considered functionally, the reference beam path and the measurement beam path are similar in configuration. In this situation, the reference beam and the measurement beam are produced by splitting of the electromagnetic radiation beam, emanating from the light source, by means of a beam divider. With this arrangement, a linear polarizer is assigned with a fixed orientation in relation to a beam-dividing analyzer. In other words, the direction(s) of transmittance of the linear polarizer(s) has/have a fixed-angle relationship to the direction of vibration of the ordinary and of the extraordinary components of the beam which are produced by means of the beam-dividing analyzers. Subsequently, the ordinary and extraordinary components of the beam are detected by means of the photosensitive sensors allocated to them.

The reference and measurement paths differ in accordance with the invention only in so far that, in the latter, the test sample is located between the linear polarizer and the beam-dividing analyzer, whereas, in the reference beam path, this position is occupied by an optically-active substance, hereinafter named the reference element, which has a known specific optical activity. Now, if the optical rotatory dispersion (ORD), as well as the temperature dependence of the optical activity of both the reference element and the substance to be analyzed, are qualitatively equal—or not capable of being differentiated within the limits of accuracy of the measurement—then the following relationship may be utilized:

$$[\alpha]_{\lambda_M}^{\theta_M} = [\alpha]_{\lambda_B}^{\theta_B} \cdot C_{\Delta\lambda} \cdot C_{\Delta\theta}$$

where:
$[\alpha]_{\lambda_M}^{\theta_M}$ = the specific optical activity at the momentary temperature and wave length $[\alpha]_{\lambda_B}^{\theta_B}$ = the specific optical activity at the reference temperature (generally 293° K.) and the reference wave length $C_{\Delta\lambda}$ = correction factor determined by the deviation of the actual wave length from the reference wave length $c_{\Delta\theta}$ = correction factor determined by the deviation of the actual temperature from the reference temperature The product of $c_{\Delta\lambda}$ and $c_{\Delta\theta}$ is determined in the reference beam path and it is used to correct the current measurement value. Accordingly, the measurement value is free from the influences occasioned by changes in the temperature and the wave length. This advantage is also shared by the saccharimeter which is chiefly used in the sugar industry. In this instrument, the rotation of the direction of vibration due to the test sample is compensated for by means of a quartz wedge. Since quartz and most sugars have practically the same dependence of their optical activity on the ORD and the temperature (compare, for example, Icsuma Proceedings, 17th Session, Montreal 1978), the compensation location of the quartz wedge is a direct measure of the optical activity of the test sample, independent of fluctuations of temperature and wave length. This property is the foundation of the reliability of the saccharimeter, even when the environmental conditions are unfavorable.

In accordance with this present invention, the aforenamed advantages are now attainable in other fields of application. This is because of the possibility of using any desired reference element, that is to say, it is always possible to select the ideal reference standard for the measurement arrangement.

The beam-dividing analyzers consist of a birefringent material, in which case the two part beams emerge from the element at different locations. For this purpose, use is made preferentially of a Foster beam divider because, with this divider, the angle of divergence between the two emergent radiation components is independent of the wave length of the incident radiation. The portion of radiation which passes straight through such a double prism is better than 99.99995% polarized, but the totally-reflected portion of the radiation is only partly polarized because of crosstalk effects.

If a source of radiation with a wave length in the visible spectrum is used, then the degree of polarization of the radiation component passing straight through, at least within the range of $+/-4$ angular degrees, is independent of the angle of incidence of the radiation impinging on the birefringent element.

In the determination of the plane of vibration of the linearly polarized light, the teachings of the invention, as are those of the generically-similar PCT/EP84/00050, are based upon the Malus Law (compare Ellipsometry and polarized light, R. M. A. Asam, N. M. Bashara, 1977, page 110). From this it is known that the intensity following an ideal analyzer may be determined from the following relationship:

$$A = A_o \cdot \cos^2 \alpha \cdot C$$

where:
A = the measured intensity after the analyzer
$A_o$ = the incident intensity
$\alpha$ = the angle between the incident linearly-polarized radiation and the transmittance direction of the analyzer
C = constant factor determined by the reflection losses on entry and emergence of the radiation as well as the absorption of the analyzer material.

By solving of the above equality for $\alpha$, the following relationship is established:

$$\alpha = \arccos \sqrt{\frac{A}{A_o} \cdot \frac{1}{C}}$$

The majority of beam-dividing crystal polarizers are, within the range of the measurement accuracy, ideal polarizers for both radiation components. Therefore it is possible to use the Malus Law for both radiation components. As already discussed, in the case of a Foster beam divider, it is only the radiation component passing straight through which is polarized to an adequate extent. Accordingly, it is only its output intensity which follows the Malus Law and may be used to determine the value of A.

For the further processing of the output signal from the photosensitive sensor and the output of the physical values assignable to the polarization state of the electromagnetic radiation, a measuring circuit is coupled-in after the photosensitive sensors.

The teachings of this present invention are now based upon the fact that the value of the product $C \cdot A_o$ may be determined from the following relationship:

$$C \cdot A_o = A_T + A_D$$

where:
- $A_o$ = the energy of the light before the birefringent element
- $A_T$ = the energy of the totally-reflected radiation component
- $A_D$ = the energy of the transmitted radiation component
- C = constant factor.

The above relationship also applies for the Foster beam divider, because the sum of the intensities of the two part beams is always independent of the direction of polarization of the incident radiation. In accordance with the above relationship, the sum of $A_T$ and $A_D$ is first of all determined by means of an addition-circuit which is coupled-in after the temporary storages. The output value from the addition-circuit is accordingly directly proportional to the energy of the light from the birefringent element.

Subsequently, with the aid of a division-circuit, which is connected on its input side to the output of the addition circuit and the output of one of the two temporary storages, the ratio of the intensity of the part beam which is allocated to the relevant temporary storage, that is to say, the value A, to the output value from the addition-circuit, that is to say, the value $A_o \cdot C$, is determined. The standardized value obtained in this way is then fed into the digital data-processing device for further processing in real time.

In a preferred form of embodiment of the measurement arrangement in accordance with the invention, there is an amplifier coupled-in before each of the temporary storages and it is programmable with respect to amplification. For this purpose, use is made preferably of the so-called instrumentation amplifiers, in which the resistance determining the amplification may be altered by means of a resistance- and switching-network. Under these conditions, the switching networks are controlled by way of a second control circuit. Differing absorptions of the test samples may be compensated for in this way in specified steps which are defined by the values of the resistances in the resistance network.

The advantage achieved thereby resides in the fact that it is only the analog components before the instrumentation amplifier, that is to say, the photosensitive sensors and their input-operations-amplifiers, which must suffice for the desired resolution and the accuracy multiplied by the required dynamic range, which arises from the various absorptions of the test samples. In contrast to this, all of the analog components coming after the instrumentation amplifier have to be sufficient only for the desired measurement accuracy.

If, for example, it is required to have a resolution and accuracy of the measurement results of 0.01 angular degrees, and if substances are to be able to be investigated which have an absorption up to log. density 2, then the analog components coming after the instrumentation amplifier should have a maximal non-linearity of 15 ppm, and the value for those coming in front of the instrumentation amplifier should be 0.15 ppm. This fact is of very considerable importance, because there are practically no sample/hold circuits available (here as temporary storages) which have an accuracy of 0.15 ppm. Without the measurement arrangement in accordance with the invention having the programmable instrumentation amplifier, there would accordingly be a very considerable worsening of the measurement accuracy which would have to be accepted, at least in the case of higher absorptions by the test samples.

It must be emphasized at this juncture that the instrumentation amplifiers which are programmable with respect to amplification are only necessary for the purpose of obtaining the best possible modulation of the analog components which come after them, with the objective of preserving linearity characteristics at higher test sample absorptions. However, because of the division circuit, the measurement results are fundamentally uninfluenced by the alterations of the output intensity of the light source and differing absorptions of the test samples.

On the basis of the unavoidable resistance tolerances in the resistance network of the programmable instrumentation amplifier, inequalities in the degree of amplification rise between the instrumentation amplifiers.

In order to be able to determine these inequalities, in accordance with the invention switching-circuit elements are provided, before each instrumentation amplifier, with which it is possible to provide a calibrated voltage to the inputs of the instrumentation amplifiers. These switching-circuit elements are controlled by means of a third control circuit allocated to them.

The calibration process functions in essentially the following manner:

First of all, the amplification of the instrumentation amplifier is programmed to the value 1 by means of the second control circuit. Following this, the switching-circuit elements supply a calibrated voltage to the inputs of the instrument amplifier with such a value that the following components can be fully modulated over the whole of their dynamic range. The signal arriving at the analog-digital converter is thereupon digitalized and the information so obtained is put into a storage device. In the following steps, the amplification is set to the next higher value and the foregoing procedure is repeated until all of the amplification stages have been encompassed.

The stored values, correlating to each of the amplification stages, which have been obtained in this manner are then calculated as correction factors with the measured value currently under consideration, corresponding to the immediately adjusted amplification stage.

Furthermore, the offset may be determined by having the calibrating voltage set at the value of 0 volt.

The calibration procedure which has been described in the foregoing may also be effected while the measurement program is running. Accordingly, all of the drifts are detected and correspondingly the correction factors are actualized.

In an especially preferred form of embodiment of the measurement arrangement in accordance with the invention, the required calibration voltages are produced by means of digital/analog converter. Associated with this, there is the additional advantage that a plurality of different voltage values may be applied to the inputs of the instrumentation amplifier, by which means the linearity behavior of the analog components may be determined. Thus, for example, it is possible, after the switching on of the measurement system, to detect hidden errors within the analog circuitry by means of a subsequent systems-test.

In another preferred form of embodiment of the measurement arrangement in accordance with the invention, the voltage at the outputs from the photosensitive sensors is utilized to generate the calibration voltage. Under these conditions, there is then only a calibration cycle when—and this is dictated by the absorption due to the test sample—the instrument amplifier has to be switched over to a different amplification stage, that is to say, actually only in the situation where a calibration voltage is available. In order to be able to determine here the offset of the components following the instrumentation amplifier, the switching-circuit elements are designed in such a way that the inputs of the instrumentation amplifier can also be connected with the analog ground potential.

The dynamic range of the measurement system, that is to say, the maximum admissible optical density of the test sample, for which the accuracy of the measurement results still lies within the tolerance limits determined by the electronic components is, in accordance with the invention as described previously, considerably widened by the use of the instrumentation amplifiers. According to patent claim 7, a utility supply unit is provided for the control of the optical output voltage of the source of radiation, which is connected on the input side to the digital data-processing device and on the output side to the source of radiation. In this way, there is achieved an additional widening of the dynamic range, which is then able to cope with even the most extreme demands, for example in the analysis of dark-colored sugar juices in the sugar industry.

In the investigation of optically-active substances, it is possible, for example, to use an impulse radiation source for generating the measurement beam. This has the advantage of being able to supply very high output voltages over short periods of time. In order to be able to guarantee the best possible exploitation of the working mode of the impulse radiation source in combination with the measurement arrangement in accordance with the invention, the synchronisation- or trigger-input of the utility supply unit is connected to the output of the control circuit allocated to the temporary storages. This measure makes possible a simultaneous, synchronous working mode of the impulse radiation source and the measurement circuitry, under which conditions it is possible to achieve measurement times in the submicrosecond range.

Yet another embodiment of the invention enables photometric analyses to be carried out. For this purpose, it is necessary to be able to establish the absolute intensity of the light beam which is to be analyzed, in particular quite independently of the polarization state. As already described, the output value from the addition-circuit of the measurement branch is a direct measure of the intensity of the measurement beam.

For the evaluation of this signal, provision is made in accordance with the invention to have a device for the selectable direct connection of the output of this addition-circuit to the measurement input to the analog/-digital converter with the masking of the remaining signals from the measurement input to the analog/digital converter.

WAYS IN WHICH THE INVENTION MAY BE IMPLEMENTED

FIG. 1 depicts an embodiment of the measurement arrangement in accordance with the invention for the optical section, and this will be described in more detail in what follows.

The radiation source 2, for example a xenon photoflash lamp or an impulseIR-diode, which is connected to the utility supply unit 1, generates a main beam H. This impinges upon a 45-degree Foster beam divider (beam-dividing polarizer) 3 which separates the ordinary radiation component (totally-reflected portion) R from the extraordinary radiation component (portion transmitted straight through) M.

The reference beam R is subsequently polarized, for example by means of a Glan polarizer 4, before it passes through a quartz crystal 5 which is appropriately cut in relation to the axis, and which represents the optically-active reference element. In a second 45-degree Foster beam divider (first beam-dividing analyzer) 6, the reference beam R is then split into a so-called additive beam (totally-reflected portion) 'a' and a so-called test beam (portion passing straight through) 'b'. Both these beam components a, b are then picked-up quantitatively by means of a photosensitive sensor 7, 8 respectively.

The measurement beam M which is produced by the beam-dividing polarizer 3 passes through test-sample chamber 9 and this likewise impinges upon a third 45-degree Foster beam divider (second beam-dividing analyzer) 10. Again, this splits the measurement beam M into the additive beam 'c' and the test beam 'd'. Here too, there is a large-surface photosensitive sensor 11, 12 allocated to each of the radiation components c, d respectively.

Figure 2:
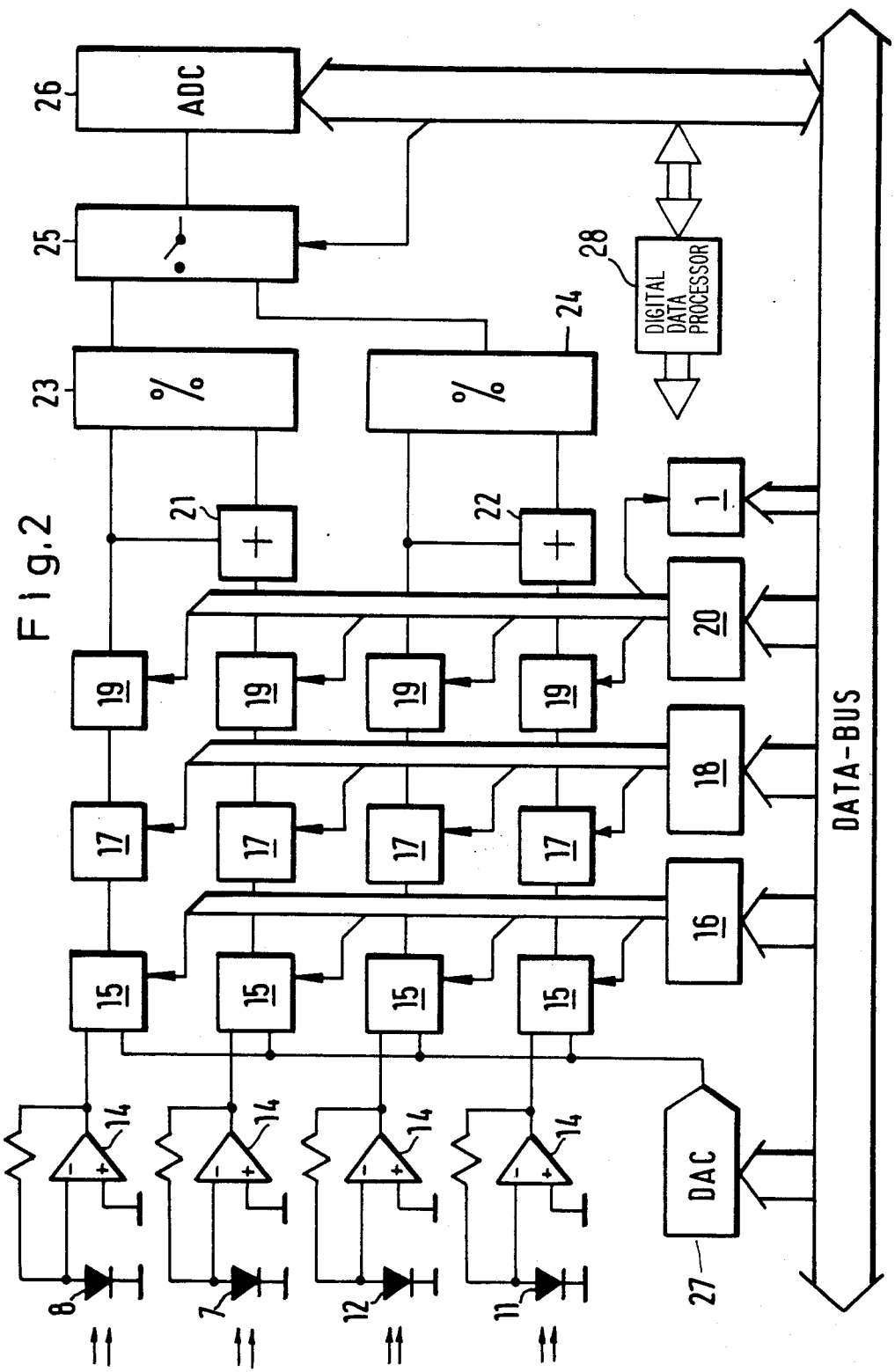
FIG. 2 depicts an embodiment of the measurement circuit of the invention.

An example of embodiment of the measurement circuit is shown in FIG. 2.

All the photosensitive sensors 7, 8, 11, 12 are connected to the input-operations amplifiers 14, which are preferably fabricated by means of FET-technology (FET=field-effect transistor). Voltages are present at their outputs, the values of which are directly proportional to the intensities of the radiation incident upon the photosensitive sensors 7, 8, 11, 12 which are respectively allocated to the relevant input-operations amplifier 14. Each output of the input-operations amplifiers 14 referred to above passes by way of a switching-circuit element 15 to the input of one of the instrumentation amplifiers 17 which has been programmed for amplification. The switching-circuit elements of each channel are connected to the outputs of the third control circuit 16, and thus they are programmed by way of the digital data-processing device. The instrumentation amplifiers 17 themselves are controlled in their amplification by means of the second control circuit 18. The outputs of the instrumentation amplifiers 17 are connected to the inputs of the sample/hold circuits 19 allocated to them, which here assume the function of temporary storages. Their synchronous control is taken over by the first control circuit 20.

The sample/hold circuits 19 which are allocated to the photosensitive sensors 7 and 8 are connected at their output side with the inputs of a first addition-circuit 21. The output signal of the first addition-circuit 21 is further fed into a first division-circuit 23. Its second input is coupled to sample/hold circuit 19 which is allocated to the photosensitive sensor 8. Accordingly, there is a voltage signal present on this line which is directly proportional to the intensity of the part beam 'b' which passes straight through the first beam-dividing analyzer 6. In other words, a signal is available at the second input of the division circuit 23, with said signal following the Malus Law and therefore it may be used for determining the value of A.

In an analogous manner, the output signals derived from the sample/hold circuits 19 allocated to the photosensitive sensors 11, 12 are supplied to a second division-circuit 24 by way of a second addition-circuit 22.

The outputs of the two division-circuits 23, 24 lead to the inputs of a CMOS-circuit 25, the output of which, in its turn, is connected to the measurement input of an analog/digital converter 26. Furthermore, the control input of the CMOS-circuit is connected to the digital system bus. In this way it is selectively possible to switch the first division-circuit 23 or else the second division-circuit 24 through to the analog-digital converter.

The output signals from the two division-elements are selectively supplied to a digital data processing device 28 through at least one analog-digital converter 26. The digital data processor 28 permits further processing of the measurement signals in real time. That is, the digital data processor 28 provides for computation and output of the polarization state of the physical magnitudes assignable to the electromagnetic radiation, and has its input connected to both of the division circuits 23 and 24 through the analog-digital converter 26.

By means of an digital to analog converter 27, it is possible to supply defined voltages for calibration of the whole of the circuitry to the inputs of the instrumentation amplifier 17 by way of the switching elements 15 which have already been described. This calibration takes place automatically at certain specified intervals of time, in order to be able to detect any possible drift of the constructional components and to compensate for them in the computations.

In order to be able to control the light source 2 synchronously with the temporary storages (19) (sample/-hold circuits), the trigger input of the utility supply unit 1 of the light source 2 is likewise connected to the control outputs of the first control circuit 20. Furthermore, for control of output voltage of the light source 2, its utility supply unit 1 is directly connected to the digital data-processor.

We claim:

1. (a) Device for measurement of the rotation of the plane of vibration of linearly polarized electromagnetic radiation, or of physical magnitudes derivable therefrom, in which case:
    (b) the said radiation, after interaction with the substance to be investigated, impinges upon a stationary beam-dividing analyzer providing two part beams (c, d) (10),
    (c) the part beams (c, d) which emerge from the beam-dividing analyzer each impinge upon separate photosensitive sensors (11, 12), and
    (d) the outputs of the photosensitive sensors (11, 12) are connected to a measurement circuit, characterized in that
    (e) the electromagnetic radiation, before interaction with the substance to be investigated, is split up into a measurement beam moving along a measurement beam path (M) and a reference beam moving along a reference beam path (R),
    (f) the reference beam (R) after interaction with a reference element (5) impinges upon a first beam-dividing analyzer (6),
    (g) the measurement beam (M) after interaction with the test-sample (9) to be investigated impinges upon a second beam-dividing analyzer (10),
    (h) the beam-dividing analyzers (6, 10) consist of a birefringent material, in which case the two part beams (a, b, c, d) emerge from the elements at different positions,
    (i) the measurement circuit is designed for processing the output signals of the photosensitive sensors (7, 8, 11, 12) of both beam-dividing analyzers (6, 10), and
    (j) the measurement circuit possesses
        (j.1) a temporary storage (19) located after each photosensitive sensor (7, 8, 11, 12) with an allocated first control circuit (20), for the synchronous, temporary, storage of the output signals of the photosensitive sensors (7, 8, 11, 12),
        (j.2) an addition-circuit (21, 22) allocated to each beam path, the input side of which is connected to the outputs of the temporary storage (19) which is currently associated with the beam path concerned,
        (j.3) one delay-free operating division-circuit (23, 24) with its input side connected to the output of one of the two addition circuits (21, 22) respectively and to the output of one of the two temporary storages (19) which is currently allocated to it,
        (j.4) a digital data-processor for computation and output of the polarization state of the physical magnitudes assignable to the electromagnetic radiation, in which case its input side is connected to the output of both the division-circuits (23, 24), and
        (j.5) at least one A/D-converter (26) coupled-in before the digital data-processor.

2. The measurement arrangement according to claim 1, characterized in that the electromagnetic radiation emanating from the source of radiation (2) is split into a reference beam (r) and a measurement beam (M) by means of a beam-dividing polarizer (3).

3. The measurement arrangement according to claim 1, characterized in that each of the temporary storages (19) has an amplifier (17), which is programmable with respect to its amplification and has a second control circuit (18) allocated to it, coupled-in before it.

4. The measurement arrangement according to claim 3, characterized in that, for the calibration of the analog components, each of the programmable amplifiers (17) has a control element (15), with a third control circuit (16) allocated to it, by means of which a calibration voltage may selectably be switched through for interconnection.

5. The measurement arrangement according to claim 4, characterized in that use is made of a digital/analog converter (27) for generating the calibration voltage.

6. The measurement arrangement according to claim 4, characterized in that use is made of one of the voltages applied to the outputs of the photosensitive sensors (7, 8, 11, 12) for generating the calibration voltage, and the switching elements (15) are designed also for connection of the inputs of the programmable amplifier (17) to the analog ground potential.

7. The measurement arrangement according to claim 1, characterized in that, for the control of the output voltage of the radiation source (2), a utility supply unit (1) is provided which is connected on the input side with the digital data-processor and on the output side to the radiation source (2).

8. The measurement arrangement according to claim 1, characterized in that, with the use of a pulsed radiation source (2), for its synchronization with the temporary storages (19), the trigger input of the utility supply unit (1) is also connected to the output of the control circuit (20) which is allocated to the temporary storages (19).

9. The measurement arrangement according to claim 1, characterized in that, for the determination of the photometric magnitudes assignable to the test sample to be analyzed, a device is provided for the selectable direct connection of the output of the addition-circuit (22) to the measurement input of the A/D-converter (26) and for the masking-off of the rest of the signals from the measurement input of the A/D-converter (26).

* * * * *